United States Patent [19]

Tsuji

[11] 4,181,683

[45] Jan. 1, 1980

[54] 1,7-OCTADIEN-3-ONE AND PROCESS FOR PREPARING THE SAME

[75] Inventor: Jiro Tsuji, Kamakura, Japan

[73] Assignee: Mitsubishi Petrochemical Co., Ltd., Tokyo, Japan

[21] Appl. No.: 949,362

[22] Filed: Oct. 6, 1978

[30] Foreign Application Priority Data

Oct. 11, 1977 [JP] Japan .................. 52-120925

[51] Int. Cl.$^2$ ............................................ C07C 49/20
[52] U.S. Cl. ............................. 260/593 R; 260/586 C; 260/586 F
[58] Field of Search ...................... 260/593 R

[56] References Cited

PUBLICATIONS

Hickinbottom, "Rxns of Organic Compounds", pp. 131-134 (1957).
Fieser et al., "Reagents for Organic Synthesis", pp. 630-640 (1967).

*Primary Examiner*—James H. Reamer
*Attorney, Agent, or Firm*—Sughrue, Rothwell, Mion, Zinn and Macpeak

[57] ABSTRACT

1,7-Octadien-3-one of the formula:

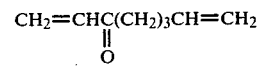

and a process for preparing the same by oxidizing 1,7-octadien-3-ol.

1 Claim, No Drawings

1,7-OCTADIEN-3-ONE AND PROCESS FOR PREPARING THE SAME

BACKGROUND OF THE INVENTION

1. Field of the Invention

This invention relates to 1,7-octadien-3-one which is a novel compound useful as an intermediate for the synthesis of medicines, perfumes, etc., and a process for preparing the same.

2. Description of the Prior Art

Belgian Pat. No. 660,099, Aug. 23, 1965 discloses the preparation of 4,5-octadien-2-one and 3,5-octadien-2-one by treating secondary propargyl alcohols with an enol ether or a metal in the presence of acid and heat rearranging the products. Leraux et al, *Ann. Chim.* (Paris) 1968 [14]-3(2), 133-144 (Fr). discloses 2,4-octadien-6-one.

Recent advancement of the chemistry surrounding the use of metal complexes has been so great that a number of new reactions have been discovered in the last 15 or so years. Although these reactions may prove to be a useful means for organic synthesis, they are still on a theoretical level and have not been utilized to their fullest.

Various attempts have been made to utilize these new reactions or reaction products for organic synthesis and create a new route for the synthesis of useful chemical substances, and as a result, this invention has been accomplished.

SUMMARY OF THE INVENTION

Accordingly, an object of this invention is to provide 1,7-octadien-3-one of the formula:

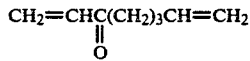

Another object of this invention is to provide a process for preparing 1,7-octadien-3-one by oxidizing 1,7-octadien-3-ol of the formula:

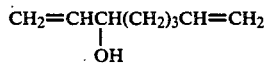

DETAILED DESCRIPTION OF THE INVENTION 1,7-Octadien-3-ol, Compound (III), which is the starting material for preparing 1,7-octadien-3-one of this invention can easily be synthesized by dimerizing butadiene using a palladium complex as a catalyst in the presence of acetic acid to obtain 3-acetoxy-1,7-octadiene, Compound (I), and then hydrolyzing the same. (See *Tetrahedron Letters*, No. 26, page 2451, 1967 incorporated herein by reference which teaches the synthesis of 4-acetoxy-2,7-octadiene and 1-acetoxy-2,7-octadiene by dimerizing butadiene in the presence of a bis(triphenyl phosphine) (maleic anhydride) palladium catalyst and acetic acid at 120° C.)

The 1,7-octadien-3-ol is synthesized by the following reaction formulae.

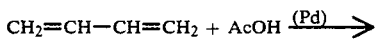

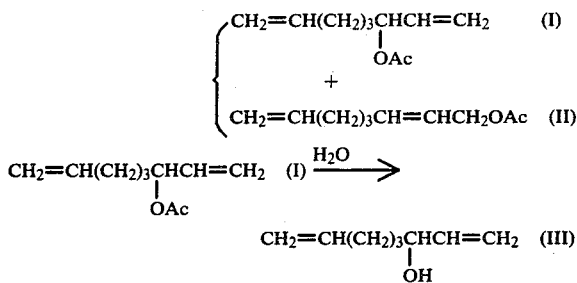

Compound (II), produced at the same time in the above reaction can easily be isomerized to its 3-acetoxy form, Compound (I), via allylic rearrangement using the palladium complex as the catalyst. Although an equilibrium is reached between Compounds (I) and (II) in the presence of the palladium catalyst, Compound (I) has a lower boiling point than that of Compound (II). Accordingly, Compound (II) can be recovered from the reactor in the form of Compound (I) by adding the palladium catalyst such as palladium acetate/triphenyl phosphine to a mixture of Compounds (I) and (II) and continuously distilling off Compound (I) at a reduced pressure while isomerizing Compound (II) into Compound (I) at a temperature of about 70° to 100° C.

Compound (I) in the above reaction formulae can easily be hydrolyzed under conventional hydrolysis conditions in the presence of an equivalent or catalytic amount of an alkali or an acid. Water or an alcohol may be used as a solvent for the hydrolysis.

The compound, 1,7-octadien-3-one, of the present invention is prepared by oxidizing 1,7-octadien-3-ol. Conventional oxidation conditions for secondary alcohols or an allylic alcohol can be employed without any substantial modification. Suitable examples of the oxidizing agents which can be used in this invention include chromic anhydride, a complex of chromic acid and pyridine, t-butyl chromate, N-halocarboxylic acid amides and imides, 2,3-dichloro-5,6-dicyano-1,4-benzoquinone (DDQ), aluminum t-butoxide, manganese dioxide, silver carbonate, cupric oxide, nickel peroxide, oxygen, etc.

Suitable examples of the solvent for oxidation which can be used in this invention include water, acetic acid, acetone, ether, benzene, pyridine, dimethyl formamide, hexamethylphosphorous triamide, methylene dichloride, chloroform, carbon tetrachloride, etc.

The oxidation is carried out at a temperature from −50° to 150° C., preferably 0° to 50° C. All necessary reactants may be mixed together before starting the reaction, or alternatively, either 1,7-octadien-3-ol or the oxidizing agent may be added stepwise to control the reaction rate.

The amount of the oxidizing agent used varies depending on its kind, but a suitable amount thereof ranges from an equivalent amount to about 30 molar times the 1,7-octadien-3-ol.

The solvent may be used in an amount up to about 50 times the weight of 1,7-octadien-3-ol depending on the type of the reactor used, reaction conditions, etc.

The compound of this invention can also be synthesized by vapor phase catalytic oxidation of 1,7-octadien-3-ol. The vapor phase catalytic oxidation (i.e., dehydrogenation reaction) is generally carried out by contacting 1,7octadien-3-ol with a molecular oxygen containing gas, such as air in the presence of a metal catalyst such as a copper/zinc alloy at a temperature of from 200° C. to 350° C. under reduced pressure to atmospheric pressure, preferably under reduced pressure.

The compound, 1,7-octadien-3-one, of this invention is a highly reactive α, β-unsaturated ketone containing a terminal vinyl group conjugated with a carbonyl group, which easily undergoes a Michael addition reaction, and is therefore useful as an intermediate for the synthesis of various organic compounds. This compound (V) to a methyl ketone group thereby producing Compound (VI) in a high yield. Subsequent aldol condensation of Compound (VI) gives Compound (VII). In this regard, see R. E. Gawley, Synthesis, No. 12, Dec., 1967, pp. 777-794 and particularly p. 794 wherein Compound (VII) is synthesized from octa-7-ene-2,6-dione via Compound (VI) intermediate through a bis Robinson Annelation. The details of the above reaction are shown in the reaction formulae given below and Application Examples 1 to 3 described hereinafter.

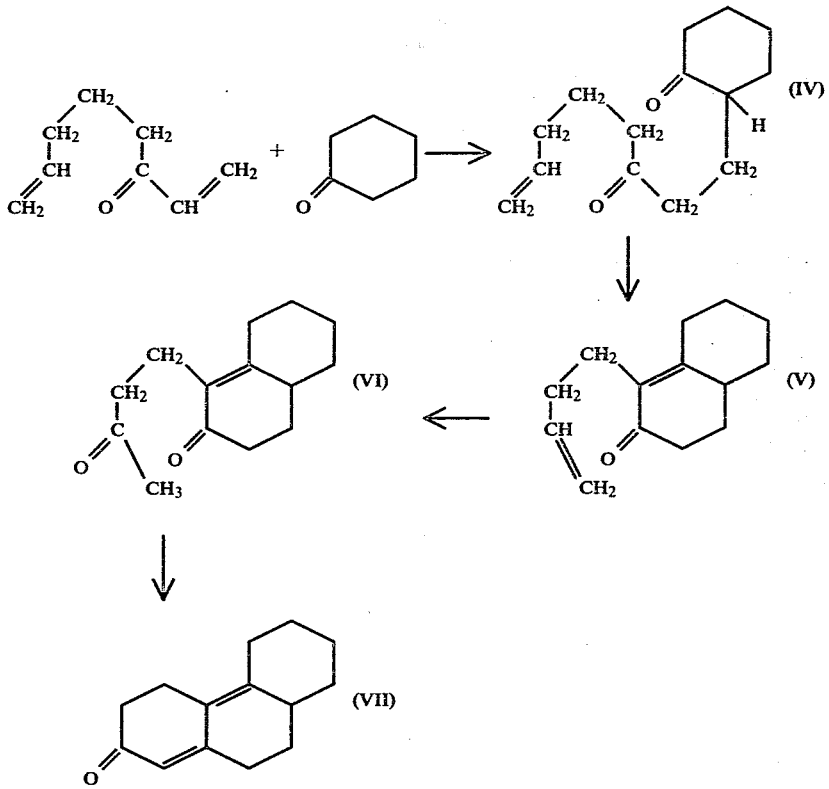

pound further contains another unconjugated terminal vinyl group. The unconjugated terminal vinyl group undergoes no change at all under conditions of Michael addition or aldol condensation of the conjugated vinyl group and, therefore, the unconjugated vinyl group can be easily converted to various groups, especially a methyl ketone group, after Michael addition and aldol condensation of the conjugated vinyl group. Thus, the compound of this invention can advantageously be used for synthesis of a wide range of compounds, particularly polycyclic compounds (e.g., by bis-annelation see Gawley, infra).

The reaction formula given below describes the reaction of 1,7octadien-3-one with cyclohexanone, wherein through a Michael addition reaction with cyclohexanone, 1,7-octadien-3-one is easily converted to Compound (IV), which is further converted to Compound (V) through an aldol condensation reaction. The terminal vinyl group of Compound (V) can be converted to various groups, of which a methyl ketone group is particularly useful. Compound (VI) contains a methyl ketone group.

Various methods are available to convert Compound (V) to Compound (VI) (oxidation). The Wacker reaction using PdCl₂ is particularly advantageous. This method converts the terminal vinyl group of Com- Similar to the above described reaction formulae, the compound of this invention can be reacted with 1-methyl-bicyclo(4,3,0)-nona-2,7-dione to synthesize an estrogen compound.

Syntheses of Compound (VI) illustrated above and an estrogen compound are only one example for the application of the compound according to this invention. Many other useful compounds can be synthesized from 1,7-octadien-3-one by relying upon the reactivity of α, β-unsaturated ketone and terminal vinyl group. In particular, the compound can advantageously be used for the synthesis of various polycyclic compounds such as steroid compounds, terpene compounds, alkaloid compounds and the like. The commercial value of 1,7-octadien-3-one is even further increased by the fact that the 1,7octadien-3-one per se can easily be synthesized from butadiene which is readily and abundantly available on an industrial scale.

This invention is now described in greater detail by the following Synthesis Example, Examples 1-3 and Application Examples 1-2. Unless otherwise indicated, all parts percents and the like are by weight.

SYNTHESIS EXAMPLE

1,7-octadien-3-ol Compound (III)

A mixture of 81 g of butadiene, 60 g of acetic acid, 100 g of triethylamine, 450 mg of palladium acetate and 1 g of triphenylphosphine was charged into a 500 cc autoclave, and reacted at 90° C. for 5 hours.

The reaction product was distilled, and 110 g of a mixture of 3-acetoxy-1,7-octadiene (I) and 1-acetoxy-2,7-octadiene (II) (weight ratio: 1:3) was obtained at 90°14 110° C./25 mm Hg.

Compound (II) was dissolved in t-butyl alcohol, and the resulting solution was heated at 80° C. for 3 hours in the presence of a catalyst comprising palladium acetate and triphenylphosphine whereby a portion of Compound (II) was isomerized to Compound (I) to isolate Compound (I) by distillation. By repeating the procedure of isomerization and distillation, the whole of Compound (II) could be isomerized to Compound (I).

20 g of Compound (I) obtained was added to a mixed solution of 100 cc of water containing 12 g of sodium hydroxide and 50 cc of ethanol, and the mixture was hydrolyzed with stirring at room temperature for 4 hours.

The hydrolyzate was distilled under reduced pressure to obtain 14 g (yield 92%) of 1,7-octadien-3-ol compound (III) at 36°-38° C./2 mm Hg.

It was confirmed from the analysis given below that the fraction was 1,7-octadien-3-ol.

NMR (CCl$_4$ Spectral Analysis:

| δ 1.2 to 1.6 ppm | (4H, methylene) |
| 1.8 to 2.2 | (2H, allyl position) |
| 3.61 | (1H, —CHOH) |
| 3.95 | (1H, OH) |
| 4.7 to 6.1 | (6H, olefin) |

EXAMPLE 1

To 100 cc of carbon tetrachloride containing 3.1 g of 1,7-octadien-3-ol (III) was added 10 g of active manganese dioxide, and the mixture was stirred at room temperature for 4 days. After filtration, the solvent (filtrate) was distilled off at a reduced pressure of 20 to 30 mm Hg to obtain 2 g of 1,7-octadien-3-one at 30°-32° C./4 mm Hg.

It was confirmed from IR and NMR spectral analysis that the fraction was 1,7-octadien-3-one.

IR Spectral Analysis:
1695 cm$^{-1}$
1680 cm$^{-1}$
1640 cm$^{-1}$
910 cm$^{-1}$ NMR (CCl$_4$) Spectral Analysis:

| δ 0.9 to 1.8 ppm | (4H, methylene) |
| 2.49 | (2H, triplet, —CH$_2$—CO) |
| 4.7 to 6.3 | (6H, olefin) |

EXAMPLE 2

To a mixture of 3.5 g of the complex of chromic anhydride and pyridine hydrochloride and 20 cc of methylene chloride was added under stirring 1.54 g of 1,7-octadien-3-ol over 4 hours at room temperature.

The reaction product was filtered, and the residue was washed with methylene chloride. The filtrate and the wash were mixed, methylene chloride was distilled off at a reduced pressure of 20 to 30 mm Hg, and the residue was distilled in vacuum to give 1.2 g of 1,7-octadien-3-one at 30°-32° C./4 mm Hg.

EXAMPLE 3

Copper-zinc alloy catalyst in pieces of net (Cu 70%, Zn 30%) was filled in a glass reactor (diameter 2 cm, length 25 cm). The pressure of the reactor was reduced to 80 mm Hg and water was added dropwise from the top of the reactor at 260° C. for 1 hour while introducing air. Then, 3.85 g of 1,7-octadien-3-ol was added dropwise from the top of the reactor over about 10 minutes. The reaction product was collected in a trap chilled at 18° C.

After bringing the reactor to room temperature and normal pressure, the inside of the reactor was washed with methylene chloride. The reaction product and methylene chloride were combined and the mixture was dried with magnesium sulfate. Methylene chloride was distilled off at a reduced pressure and the residue was distilled in vacuum to give 2.80 g of 1,7-octadien-3-one at 31° C./4 mm Hg.

the IR and NMR (CCl$_4$) spectra of the distillate were the same as in Example 1.

APPLICATION EXAMPLE 1

Synthesis of 1-(3'-butenyl)-$\Delta^{1,9}$-2-octalone (V) from 1,7-octadien-3-one A solution prepared by dissolving 2 g of pyrrolidine-enamine of cyclohexanone of the formula

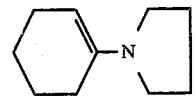

in 15 cc of dioxane was heated under reflux. To this solution was added dropwise a solution prepared by dissolving 1.24 g of 1,7-octadien-3-one in 10 cc of dioxane under reflux. The mixture was further heated with stirring for 10 hours under reflux.

The reaction product was cooled to room temperature and mixed with 15 cc of 3N-HCl, and the mixture was heated at 50° C. for 3 hours to hydrolyze the enamine.

The product was treated in a conventional manner to produce 2.1 g of an oily substance. The oily substance was a mixture of 60 wt% of Compound (IV) and 40 wt% of Compound (V).

A solution prepared by dissolving 5 g of sodium hydroxide in 100 cc of water and 25 cc of ethanol was added to the above mixture without separation, and stirred at room temperature for 2 hours. The reaction mixture was neutralized with 3N-HCL, extracted three times with 50 cc of methylene chloride, and distilled off to yield 1.42 g of a 99°-101° C./3.7 mm Hg fraction.

It was confirmed from IR and NMR spectral analysis that the fraction was 1-(3'-butenyl)-$\Delta^{1,9}$-2-octalone Compound (V).

IR Spectral Analysis:

| 1665 cm$^{-1}$ | (>C=O) |
| 1640 cm$^{-1}$ | (olefin) |
| 912 cm$^{-1}$ | (vinyl) |

NMR Spectral Analysis:

δ 4.6 to 6.1 ppm (3H, vinyl)

APPLICATION EXAMPLE 2

Synthesis of 1-(3'-oxobutyl)-Δ$^{1,9}$-2-octalone (VI) from Compound (V)

A mixture of PdCl$_2$ 0.18 g, CuCl 1 g, water 2 cc and dimethylformamide 20 cc was stirred at room temperature for 3 hours in an oxygen atmosphere and then 1.24 g of Compound (V) was added and stirred at room temperature for 24 hours in an oxygen atmosphere. The reaction product was added to 15 cc of 3N-HCl and extracted five times with 50 cc of ether.

Ether was distilled off from the extract at a reduced pressure of 20 to 30 mm Hg. The residue was distilled off to give 1.11 g of a 122°–129° C./3.5 mm Hg fraction.

It was confirmed from IR and NMR spectral analysis that the fraction was 1-(3'-oxobutyl)-Δ$^{1,9}$-2-octalone (VI).

IR Spectral Analysis:
1712 cm$^{-1}$
1663 cm$^{-1}$
NMR Spectral Analysis:

δ  2.02 ppm    (—COCH$_3$)

APPLICATION EXAMPLE 3

Synthesis of 2,3,4,5,6,7,8,9,10,14-decahydrophenanthren-2-one (VII) from Compound (VI)

230 mg of t-butoxypotassium was added to 30 cc of benzene. 472 mg of Compound (VI) was added to the mixture and heated with stirring for 3 hours under reflux.

The reaction product was washed with hydrochloric acid to isolate the organic phase and benzene was distilled off at a reduced pressure of 20 to 30 mm Hg. The residue was purified by column chromatography to obtain 250 mg of Compound (VII).

It was confirmed from IR and NMR spectral analysis that the product obtained was Compound (VII).

IR Spectral Analysis:
1660 cm$^{-1}$
1610 cm$^{-1}$
NMR Spectral Analysis:
δ 5.6 ppm (1H, singlet, olefin)

While the invention has been described in detail and with reference to specific embodiments thereof, it will be apparent to one skilled in the art that various changes and modifications can be made therein without departing from the spirit and scope thereof.

What is claimed is:

1. 1,7-Octadien-3-one of the formula:

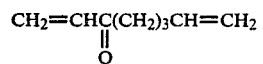

* * * * *